United States Patent
De Armas

(10) Patent No.: US 11,164,671 B2
(45) Date of Patent: Nov. 2, 2021

(54) CONTINUOUS COMPLIANCE AUDITING READINESS AND ATTESTATION IN HEALTHCARE CLOUD SOLUTIONS

(71) Applicant: International Business Machines Corporation, Armonk, NY (US)

(72) Inventor: Mario E. De Armas, Wellington, FL (US)

(73) Assignee: International Business Machines Corporation, Armonk, NY (US)

(*) Notice: Subject to any disclaimer, the term of this patent is extended or adjusted under 35 U.S.C. 154(b) by 460 days.

(21) Appl. No.: 16/253,582

(22) Filed: Jan. 22, 2019

(65) Prior Publication Data

US 2020/0234817 A1    Jul. 23, 2020

(51) Int. Cl.
*G16H 40/20* (2018.01)
*G06Q 30/00* (2012.01)

(52) U.S. Cl.
CPC ........... *G16H 40/20* (2018.01); *G06Q 30/018* (2013.01); *G06Q 2220/00* (2013.01)

(58) Field of Classification Search
CPC ...................................................... G16H 40/20
(Continued)

(56) References Cited

U.S. PATENT DOCUMENTS

| 5,864,819 A * | 1/1999 | De Armas | G06F 8/38 |
| | | | 704/275 |
| 5,873,064 A * | 2/1999 | De Armas | G06F 3/16 |
| | | | 704/275 |

(Continued)

FOREIGN PATENT DOCUMENTS

| EP | 3236374 A1 | 10/2017 |
| WO | WO2015/175722 A1 | 11/2015 |

OTHER PUBLICATIONS

List of IBM Patents or Patent Applications Treated as Related, Jan. 22, 2019, 2 pages.
(Continued)

*Primary Examiner* — Reza Nabi
(74) *Attorney, Agent, or Firm* — Stephen R. Tkacs; William J. Stock

(57) ABSTRACT

A mechanism is provided in a data processing system comprising at least one processor and at least one memory, the at least one memory comprising instructions which are executed by the at least one processor and configure the processor to implement a healthcare blockchain framework for continuous compliance auditing readiness and attestation in healthcare cloud solutions. The mechanisms provides a healthcare blockchain framework to create, read, update, and delete elements of a healthcare compliance model supporting a dynamic allocation of cloud resources to a healthcare business network. Compliance with one or more healthcare regulations is built into the blockchain framework. Responsive to an attestation event, a compliance attestation component within the healthcare blockchain framework reviews asset contents, state, and properties of an asset in a compliance repository. The compliance attestation component creates a bottom-up asset manifest for the asset and compares the asset manifest to a test case corresponding to an asset class of the asset. The compliance attestation component validates the asset against evidence rules corresponding to the asset class of the asset based on the comparison. Responsive to the compliance attestation component validating the asset, the mechanism generates a proof-of-validation certification.

20 Claims, 11 Drawing Sheets

(58) Field of Classification Search
USPC .......................................................... 726/1
See application file for complete search history.

(56) References Cited

U.S. PATENT DOCUMENTS

| | | | | |
|---|---|---|---|---|
| 8,949,998 | B2 | 2/2015 | Wong et al. | |
| 9,391,937 | B2 | 7/2016 | Murphy et al. | |
| 10,340,038 | B2* | 7/2019 | Witchey | G06F 21/00 |
| 2003/0110307 | A1* | 6/2003 | De Armas | G06F 9/546 |
| | | | | 719/310 |
| 2004/0243415 | A1* | 12/2004 | Commarford | G10L 15/26 |
| | | | | 704/275 |
| 2005/0065824 | A1* | 3/2005 | Kohan | G06Q 10/10 |
| | | | | 705/3 |
| 2007/0136814 | A1* | 6/2007 | Lee | G06F 21/552 |
| | | | | 726/25 |
| 2007/0143116 | A1* | 6/2007 | De Armas | G06F 9/505 |
| | | | | 704/270.1 |
| 2010/0218256 | A1* | 8/2010 | Thomas | H04L 63/1433 |
| | | | | 726/25 |
| 2013/0218793 | A1* | 8/2013 | Miller | G06Q 50/26 |
| | | | | 705/320 |
| 2013/0291127 | A1* | 10/2013 | Bergman | H04L 67/10 |
| | | | | 726/30 |
| 2013/0340029 | A1* | 12/2013 | De Armas | H04L 63/0245 |
| | | | | 726/1 |
| 2014/0032745 | A1* | 1/2014 | De Armas | G06F 9/542 |
| | | | | 709/224 |
| 2014/0229593 | A1* | 8/2014 | Burke | H04L 63/20 |
| | | | | 709/223 |
| 2014/0229594 | A1* | 8/2014 | Burke | H04L 41/0893 |
| | | | | 709/223 |
| 2014/0229595 | A1* | 8/2014 | Burke | H04L 41/0893 |
| | | | | 709/223 |
| 2014/0229843 | A1* | 8/2014 | De Armas | G06F 3/04842 |
| | | | | 715/739 |
| 2014/0230006 | A1* | 8/2014 | Burke | H04L 63/20 |
| | | | | 726/1 |
| 2014/0278724 | A1* | 9/2014 | Compagna | G06Q 10/0633 |
| | | | | 705/7.27 |
| 2015/0007271 | A1* | 1/2015 | Wong | H04L 63/08 |
| | | | | 726/4 |
| 2015/0106117 | A1* | 4/2015 | Ananda | G16H 50/20 |
| | | | | 705/3 |
| 2015/0106279 | A1* | 4/2015 | Gajendragadkar | G06Q 30/018 |
| | | | | 705/317 |
| 2015/0213195 | A1 | 7/2015 | Blechman | |
| 2015/0229538 | A1* | 8/2015 | Burke | H04L 47/76 |
| | | | | 709/225 |
| 2015/0332283 | A1 | 11/2015 | Witchey | |
| 2016/0071226 | A1* | 3/2016 | Karale | G16H 10/60 |
| | | | | 705/3 |
| 2016/0117471 | A1 | 4/2016 | Belt et al. | |
| 2016/0275432 | A1 | 9/2016 | Guiness et al. | |
| 2017/0019314 | A1* | 1/2017 | Chieu | H04L 41/5054 |
| 2017/0140145 | A1 | 5/2017 | Shah | |
| 2017/0373849 | A1 | 12/2017 | Donner et al. | |
| 2018/0011948 | A1* | 1/2018 | Irissou | G06F 30/30 |
| 2018/0048431 | A1 | 2/2018 | Jutla et al. | |
| 2018/0060496 | A1* | 3/2018 | Bulleit | H04L 9/3239 |
| 2019/0190958 | A1* | 6/2019 | Blitz | H04L 63/20 |
| 2019/0228133 | A1* | 7/2019 | Ansari | H04L 9/3239 |
| 2020/0028691 | A1* | 1/2020 | Rao | G06F 8/658 |
| 2020/0134190 | A1* | 4/2020 | Adam | G06F 11/3604 |
| 2020/0234816 | A1* | 7/2020 | De Armas | G06Q 10/067 |
| 2020/0234817 | A1* | 7/2020 | De Armas | G16H 40/20 |
| 2020/0250683 | A1* | 8/2020 | Padmanabhan | G06Q 20/389 |
| 2020/0410445 | A1* | 12/2020 | Blackburn | G01W 1/10 |
| 2021/0049617 | A1* | 2/2021 | Li | H04L 9/0866 |
| 2021/0166245 | A1* | 6/2021 | Novotny | H04L 9/3239 |
| 2021/0182801 | A1* | 6/2021 | O'Brien | C08J 11/06 |

OTHER PUBLICATIONS

"A Survival Guide for Enterprise Security Policy Compliance", https://www.consys.it/wp-content/uploads/2017/05/Survival_Guide_for_Enterprise_Security_Policy_Compliance_White_paper.pdf, 2016, 12 pages.

Myburgh, Mike, "Applying Blockchain to the Healthcare Industry", https://www.tibco.com/sites/tibco/files/resources/wp-applying-blockchain-to-the-healthcare-industry.pdf, Jan. 12, 2018, 6 pages.

* cited by examiner

CONTINUOUS COMPLIANCE AUDITING READINESS AND ATTESTATION IN HEALTHCARE CLOUD SOLUTIONS

BACKGROUND

The present application relates generally to an improved data processing apparatus and method and more specifically to mechanisms for continuous compliance auditing readiness and attestation in healthcare cloud solutions using a blockchain framework.

Cloud computing involves shared pools of configurable computer system resources and higher-level services that can be rapidly provisioned with minimal management effort, often over the Internet. Cloud computing relies on sharing of resources to achieve coherence and economies of scale, similar to a public utility.

Third-party clouds enable organizations to focus on their core businesses instead of expending resources on computer infrastructure and maintenance. Advocates note that cloud computing allows companies to avoid or minimize up-front Information Technology (IT) infrastructure costs. Proponents also claim that cloud computing allows enterprises to get applications up and running faster, with improved manageability and less maintenance, and that it enables IT teams to more rapidly adjust resources to meet fluctuating and unpredictable demand. The availability of high-capacity networks, low-cost computers and storage devices as well as the widespread adoption of hardware virtualization, service-oriented architecture, and autonomic and utility computing has led to growth in cloud computing.

In general, compliance means conforming to a rule, such as a specification, policy, standard or law. Regulatory compliance describes the goal that organizations aspire to achieve in their efforts to ensure that they are aware of and take steps to comply with relevant laws, policies, and regulations. Due to the increasing number of regulations and need for operational transparency, organizations are increasingly adopting the use of consolidated and harmonized sets of compliance controls. This approach is used to ensure that all necessary governance requirements can be met without the unnecessary duplication of effort and activity from resources.

Some organizations keep compliance data—all data belonging or pertaining to the enterprise or included in the law, which can be used for the purpose of implementing or validating compliance—in a separate store for meeting reporting requirements. Compliance software is increasingly being implemented to help companies manage their compliance data more efficiently. This store may include calculations, data transfers, and audit trails.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions which are executed by the at least one processor and configure the processor to implement a healthcare blockchain framework for continuous compliance auditing readiness and attestation in healthcare cloud solutions. The method comprises providing a healthcare blockchain framework to create, read, update, and delete elements of a healthcare compliance model supporting a dynamic allocation of cloud resources to a healthcare business network. Compliance with one or more healthcare regulations is built into the blockchain framework. The method further comprises responsive to an attestation event, reviewing, by a compliance attestation component within the healthcare blockchain framework, asset contents, state, and properties of an asset in a compliance repository. The method further comprises creating, by the compliance attestation component, a bottom-up asset manifest for the asset. The method further comprises comparing, by the compliance attestation component, the asset manifest to a test case corresponding to an asset class of the asset. The method further comprises validating, by the compliance attestation component, the asset against evidence rules corresponding to the asset class of the asset based on the comparison. The method further comprises responsive to the compliance attestation component validating the asset, generating a proof-of-validation certification.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
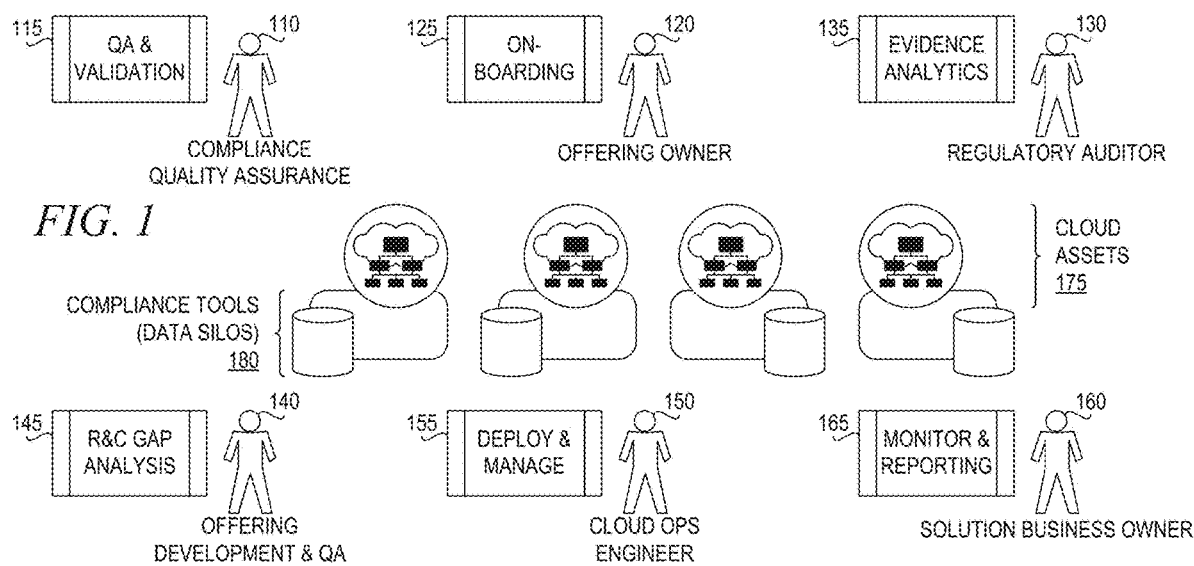
FIG. 1 illustrates a prior art healthcare reasonable and customary business network.

Companies have made a commitment and investment to transform the healthcare industry during the current era of digitization and cognitive insight. Because healthcare is such a regulated industry due to privacy, security, and sensitivity of data handled by automated solutions, a cloud platform interested in hosting healthcare workloads must overcome difficult technological challenges. Some of the challenges involve innovation in data management and cognitive insights, but many others will be more behind-the-scenes challenges, such as in the security, operational, and compliance arena. These are less obvious but nevertheless very important to the success of any cloud platform built to support a sustainable business that is compliant and secure.

Existing healthcare cloud platforms support varied and complex healthcare cloud governance rules, including the Health Insurance Portability and Accountability Act (HIPAA), "good practice" quality guidelines and regulations (GxP and QMS), General Data Protection Regulation (GDPR), security controls (SOC, ISO 27K), etc. This presents a difficult technological problem given the patchwork of tools and processes to conform with compliance requirements.

The illustrative embodiments address a key, but costly, requirement providing platform for defining, capturing, and enforcing operational GxP and Quality Management System (QMS) compliance in a healthcare life sciences regulated cloud. The current landscape of GxP/QMS cloud solutions use document management solutions that tend to solve a slice of the overall compliance needs, thus creating a lot of data silos along the way, which must be connected and reconciled to capture and validate the necessary regulatory evidence required by industry best practices.

While great advances in cloud operations, such as devops (development and operations) tools, have been invented in the last decade, the major inhibitors to operational efficiencies (e.g., agility, time, cost) become exacerbated by all the manually (i.e., human) connected trail of evidence and its validation that must be done to guarantee an auditable healthcare cloud.

The illustrative embodiments design and implement a "compliance chain" that is trusted, transparent (to the appropriate persons), and secure for all "cloud assets" involved in construction of a healthcare solution. This continuous compliance chain is possible by combining blockchain technology along with GxP/QMS healthcare cloud business network model and processes. The illustrative embodiments define the persons, processes, contracts, and data security required to support a desired level of compliance readiness that is automated and validated at scale.

An asset is any cloud entity or item (e.g., physical hardware, virtual instances, network entities/definitions, software services, environments, cloud offerings, etc.) that has value to an organization or business. A build is the process of constructing or instantiating an asset. An instance is the real identifiable and specific manifestation of an asset type or class.

The illustrative embodiments provide enforcement of continuous compliance by automating compliance rules and processes as logic in a continuous integration and continuous delivery (CICD) pipeline and baking in regulatory expertise and requirements. The illustrative embodiments leverage blockchain technology to record and audit information in a "compliance chain." For example, example embodiments may use Hyperledger fabric and smart contracts to record regulated tasks and changes during a healthcare cloud operation.

Hyperledger Fabric is a blockchain framework implementation and one of the Hyperledger projects hosted by The Linux Foundation. Intended as a foundation for developing applications or solutions with a modular architecture, Hyperledger Fabric allows components, such as consensus and membership services, to be plug-and-play. Hyperledger Fabric leverages container technology to host smart contracts called "chaincode" that comprise the application logic of the system.

Hyperledger Composer is a set of collaboration tools for building blockchain business networks that make it simple and fast for business owners and developers to create smart contracts and blockchain applications to solve business problems. Built with JavaScript, leveraging modern tools, Composer offers business-centric abstractions as well as sample apps with easy-to-test devops processes to create robust blockchain solutions that drive alignment across business requirements with technical development.

Composer is a user-facing rapid prototyping tooling, running on top of Hyperledger Fabric, which allows the easy management of Assets (data stored on the blockchain), Participants (identity management, or member services) and Transactions (Chaincode, a.k.a. Smart Contracts, which operate on Assets on the behalf of a Participant). The resulting application can be exported as a package, which may be executed on a Hyperledger Fabric instance, with the support of an application and provide a Representational State Transfer (REST) interface to external applications.

The illustrative embodiments provide compliance attestation for continuous monitoring of deployed services, comparing compliance chain records to bottom-up introspection of cloud environment state, and raising and investigating issues proactively. The illustrative embodiments provide a compliance infrastructure to create, read, update, and delete (CRUD) elements of a healthcare compliance model supporting a dynamic allocation of (cloud) resources operational design. Compliance to healthcare regulations is built into a blockchain design. The compliance infrastructure includes an automation process layer, and application programming layer supporting interfaces for managing cloud assets compliance, enabling storing of compliance evidence, and a role-based access and filtering mechanism. The illustrative embodiments utilize the compliance infrastructure to provide immutable and non-repudiation operational best practices.

The illustrative embodiments save time, remove tools and overhead costs, reduce risks from tampering or human error, and increase trust and recordkeeping. The blockchain framework of the illustrative embodiments is trusted, transparent, accountable, immutable, secure, scalable, and fast.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

FIG. 1 illustrates a prior art healthcare reasonable and customary business network. Reasonable and Customary (R&C) is a term used to refer to the commonly charged or prevailing fees for health services within a geographic area. A fee is considered to be reasonable if it falls within the parameters of the average or commonly charged fee for the particular service within that specific community. R&C creates a maximum that is allowed for a particular service based on the geographical area and the charges for the same service within that area. This data is collected, compiled and an R&C amount is determined. Also referred to as Usual and Customary, or Usual, Customary and Reasonable (UCR). A compliance quality assurance specialist 110 performs quality assurance (QA) validation (block 115). Quality assurance (QA) is a way of preventing mistakes and avoiding problems when delivering solutions or services to customers. Quality assurance comprises administrative and procedural activities implemented in a quality system so that requirements and goals for a service or activity will be fulfilled.

Offering owner 120 performs on-boarding (block 125). Onboarding is the process by which patients are welcomed and oriented into a provider's practice. Introducing new patients to the office procedures and systems helps them navigate the office and healthcare experience.

Regulatory auditor 130 performs evidence analytics (block 135). Analytics is the discovery, interpretation, and communication of meaningful patterns in data and applying those patterns towards effective decision making. In other words, analytics can be understood as the connective tissue between data and effective decision making, within an organization.

Offering development and quality assurance specialist 140 performs R&C gap analysis (block 145). Gap analysis identifies gaps between the optimized allocation and integration of resources and the current allocation level. This may reveal areas that can be improved. Gap analysis involves determining, documenting, and improving the difference between business requirements and current capabilities. Gap analysis naturally flows from benchmarking and from other assessments. Once the general expectation of performance in an industry is understood, it is possible to compare that expectation with the company's current level of performance. This comparison becomes the gap analysis. Such analysis can be performed at the strategic or at the operational level of an organization.

Cloud operations (ops) engineer 150 performs deployment and management (block 155). Solutions business owner 160 performs monitoring and reporting (block 165).

The healthcare business network is implemented using cloud assets 175. In one embodiment, cloud assets 175 include environments, offering services, virtual machines (VMs), etc. The healthcare business network also implements compliance tools 180 on the cloud assets 175; however, the compliance tools 180 are varied and complex and result in data silos. An information silo, or a group of such silos, is an insular management system in which one information system or subsystem is incapable of reciprocal operation with others that are, or should be, related. Thus, information is not adequately shared but rather remains sequestered within each system or subsystem. Information silos occur whenever a data system is incompatible or not integrated with other data systems. This incompatibility may occur in the technical architecture, in the application architecture, or in the data architecture of any data system.

Figure 2:
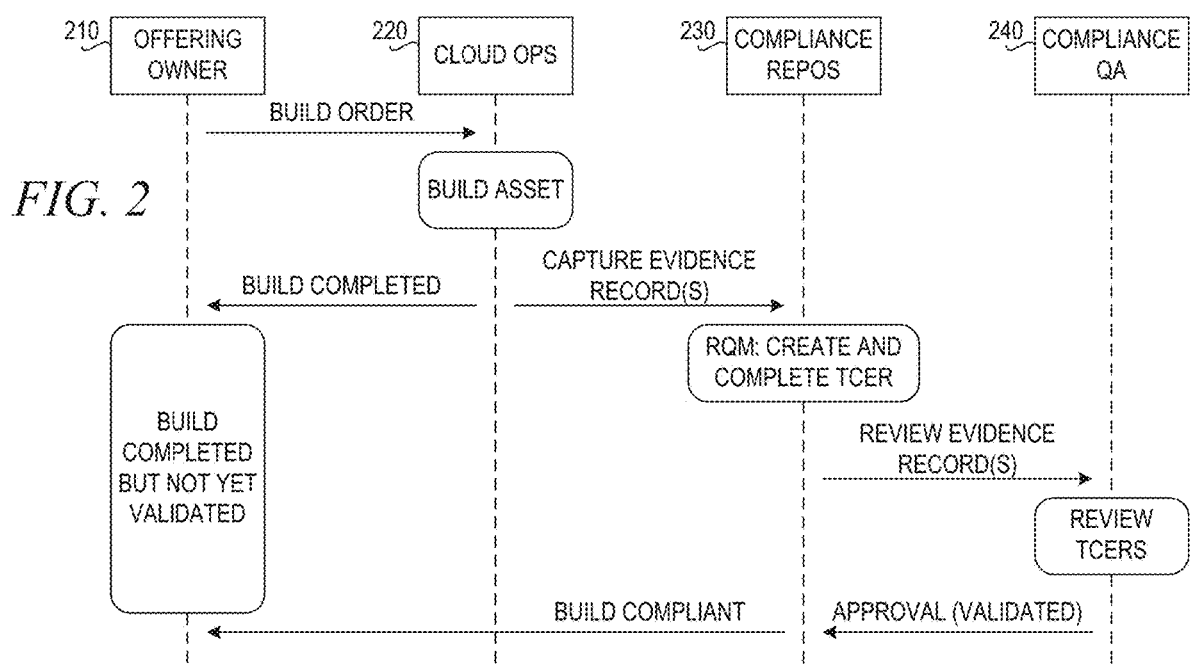
FIG. 2 illustrates a prior art validated build.

FIG. 2 illustrates a prior art validated build. In the depicted example, an offering owner 210 sends a build order to cloud operations 220, which begins to build an asset. The cloud ops 220 sends captured evidence records to compliance repository 230. At completion, cloud ops 220 sends a build completed event to offering owner 210, at which point, the build is completed but not yet validated.

At the compliance repository 230, a Rational Quality Manager (RQM) creates and completes Test Case Execution Records (TCERs). A compliance quality assurance specialist reviews the TCERs (evidence record(s)) and returns approval to the compliance repository 230. In turn, the compliance repository 230 returns a build compliant event to the offering owner, at which time the build is validated.

Figure 3:
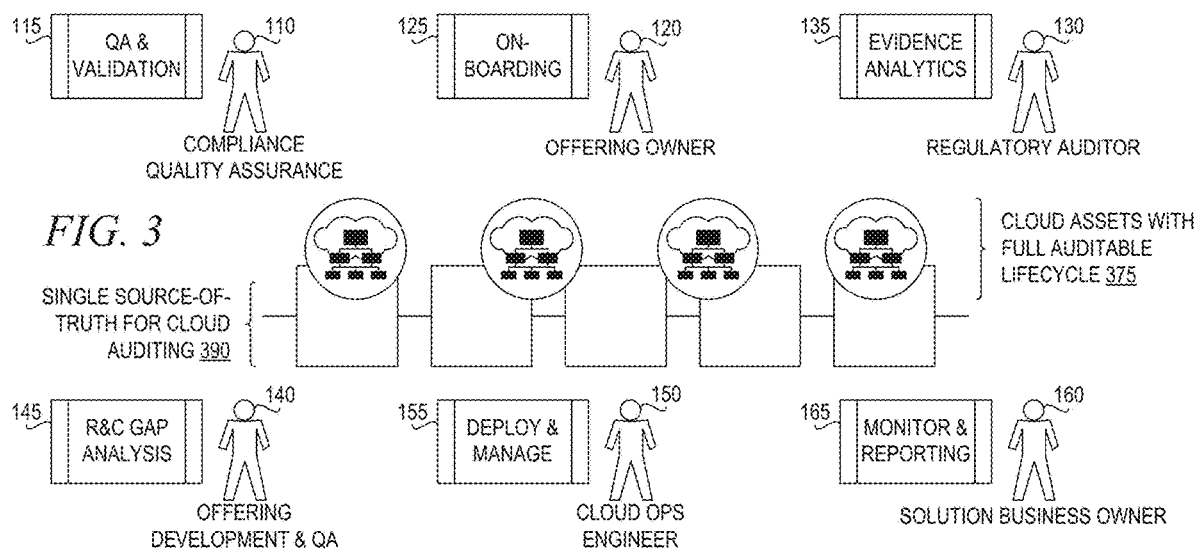
FIG. 3 illustrates a healthcare reasonable and customary business network using a blockchain framework for enforcing regulatory compliance in healthcare cloud solutions in accordance with an illustrative embodiment

FIG. 3 illustrates a healthcare reasonable and customary business network using a blockchain framework for enforcing regulatory compliance in healthcare cloud solutions in accordance with an illustrative embodiment. In the example depicted in FIG. 3, the cloud assets 375 have a full auditable lifecycle. Also, the compliance tools are implemented using a blockchain framework, providing a single source of truth for cloud auditing 390.

Figure 4:
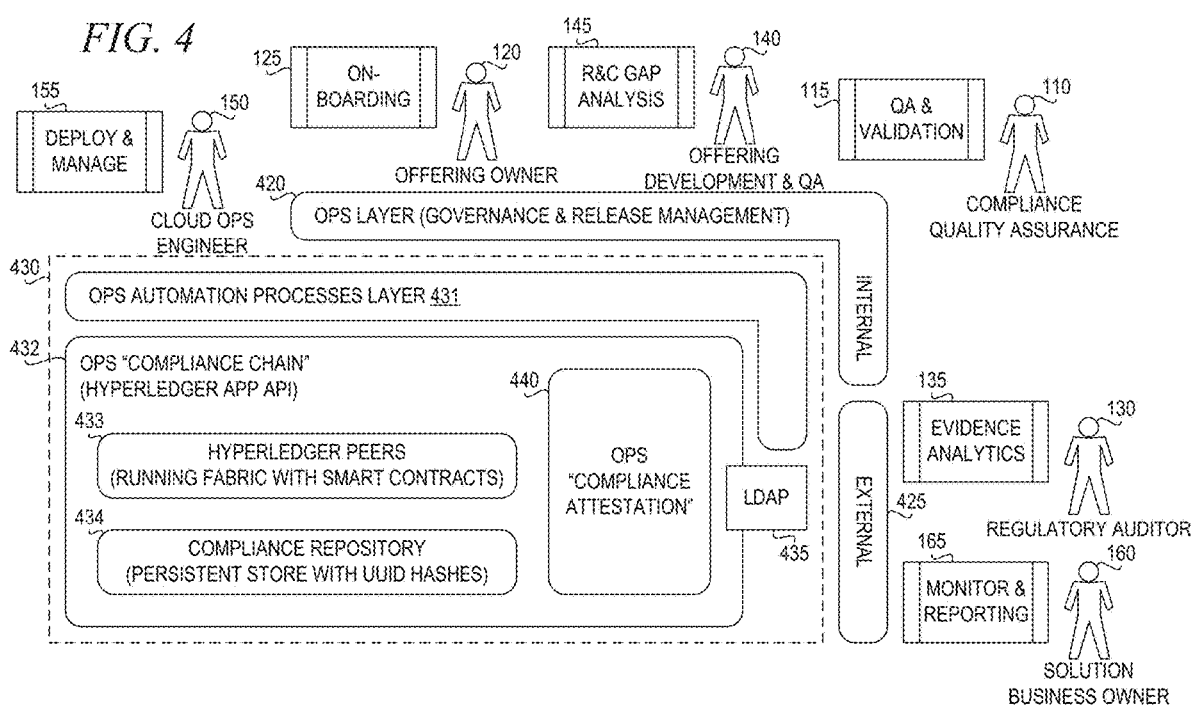
FIG. 4 is a block diagram illustrating a blockchain framework for enforcing regulatory compliance in healthcare cloud solutions in accordance with an illustrative embodiment

FIG. 4 is a block diagram illustrating a blockchain framework for enforcing regulatory compliance in healthcare cloud solutions in accordance with an illustrative embodiment. An operations layer 420 and blockchain framework 430 are internal to the healthcare business organization. Cloud ops engineer 150, offering owner 120, offering deployment and QA 140, and compliance quality assurance 110 interact with the blockchain framework 430 via the internal ops layer 420. Ops layer 420 provide governance and release management. Regulatory auditor 130 and solution business owner 160 interact with the blockchain framework 430 using an external interface 425. The blockchain framework 430 provides Lightweight Directory Access Protocol (LDAP) component 435, which is an open, vendor-neutral, industry standard application protocol for accessing and maintaining distributed directory information services over an Internet Protocol (IP) network.

Blockchain framework 430 comprises ops automation process layer 431 and ops compliance chain 432. In one example embodiment, ops compliance chain 432 is implemented using HyperLedger Application Programming Interface (API). Hyperledger Fabric is a blockchain framework implementation and one of the Hyperledger projects hosted by The Linux Foundation. Intended as a foundation for developing applications or solutions with a modular architecture, Hyperledger Fabric allows components, such as consensus and membership services, to be plug-and-play. Hyperledger Fabric leverages container technology to host smart contracts called "chaincode" that comprise the application logic of the system.

The ops compliance chain comprises HyperLedger peers 433 and compliance repository 434. HyperLedger peers run on HyperLedger Fabric with smart contracts. A smart contract is a computer protocol intended to digitally facilitate, verify, or enforce the negotiation or performance of a contract. Smart contracts allow the performance of credible transactions without third parties. These transactions are trackable and irreversible. Proponents of smart contracts claim that many kinds of contractual clauses may be made partially or fully self-executing, self-enforcing, or both. The aim of smart contracts is to provide security that is superior to traditional contract law and to reduce other transaction costs associated with contracting. Various cryptocurrencies have implemented types of smart contracts. Compliance repository 434 is a persistent store with universally unique identification (UUID) hashes. A universally unique identifier (UUID) is a large number hash used to identify globally unique information in computer systems. The term globally unique identifier (GUID) is also used. When generated according to the standard methods, UUIDs are for practical purposes unique, without depending for their uniqueness on a central registration authority or coordination between the parties generating them, unlike most other numbering schemes. While the probability that a UUID will be duplicated is not zero, it is close enough to zero to be negligible. Thus, anyone can create a UUID and use it to identify something with near certainty that the identifier does not duplicate one that has already been, or will be, created to identify something else. Information labeled with UUIDs by independent parties can therefore be later combined into a single database, or transmitted on the same channel, with a negligible probability of duplication.

Ops compliance chain 432 also comprises ops compliance attestation engine 440. Regulatory compliance evidence is collected in compliance repository 434 as part of a continuous pipeline enabled with a compliance chain. Compliance evidence gathered as part of the asset compliance chain becomes validated using predetermined test cases specific to each built asset class and instance. There is a validation test that occurs for a platform service that specifically understands and codifies checks against the platform service build out evidence looking for correlations between evidence data (logs and files) and verification tests (smoke and functional test results performed in different methods). This capability validates a build.

Furthermore, the compliance attestation engine 440 continuously monitors evidence coherence, verifies its audit robustness, and generates compliance operational alarms, as needed. The compliance attestation engine 440 uses a bottom-up method of checking what actually got built (direct asset introspection) versus what should have been built (approved published order), along with attestation checklist of all evidence that should be part of that specific built asset and included in compliance evidence chain under that unique asset's entry.

Example embodiments of compliance attestation engine 440 include, but are not exclusive to, HyperLedger smart contracts (i.e., chain code), which enforce the required capture and verification of the evidence for a specific compliance chain operation.

The compliance attestation engine 440, which registers for build order completion events and validates evidence against evidence rules coded for specific asset types and build evidence. This logic updates the asset to "validated" state when a check has been completed. Compliance attestation engine 440 generates an immutable and non-repudiating proof of validation certification for each time this step is performed. Compliance attestation engine 440 persists this certification to compliance repository 434 as a compliance chain transaction with corresponding hashed data attached to the compliance chain.

Compliance attestation engine 440 performs continuous attestation. The chain generates events whenever a change is performed and can trigger an attestation or (re-attestation) of certification based on the current state of the asset. The asset contents, state, and properties are directly introspected using third party methods (not involving the original code path that created it), creating a bottom-up asset manifest. This manifest is then compared to one created during the first attestation of the asset (when it was validated to contain expected content). If a variation from this expected content is detected, compliance attestation engine 440 generates a compliance alarm to inform the compliance owner to investigate further.

Because of HyperLedger Fabric's ability to produce a historian record of asset transactions and changes, the compliance chain attestation engine 440 evidence chain provides added level of qualification and auditing strength posture for any healthcare organization hosting a solution in a cloud platform.

Figure 5:
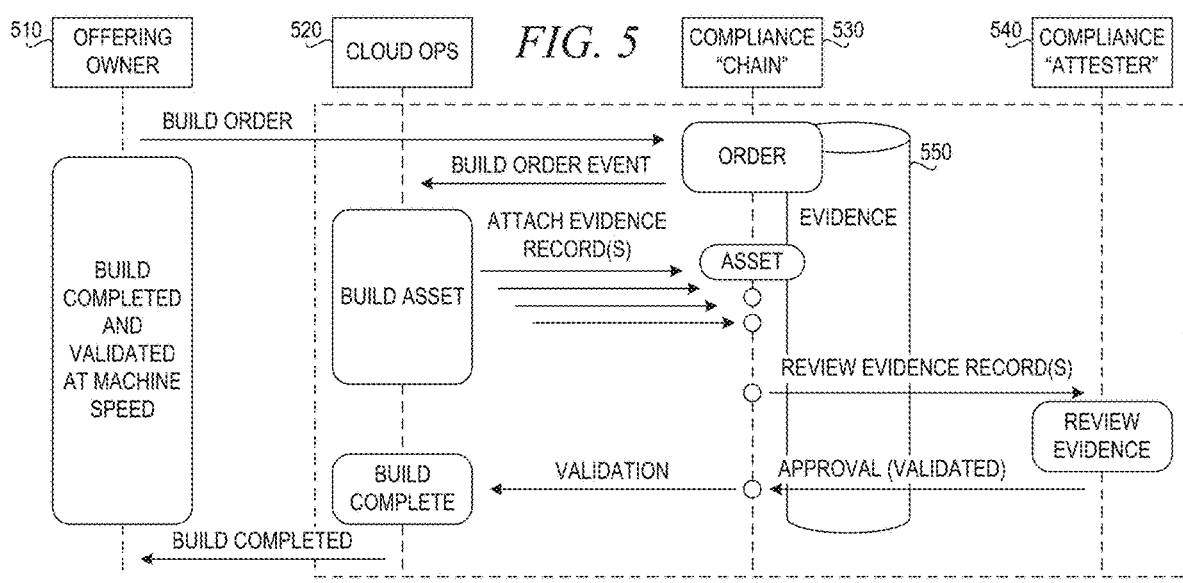
FIG. 5 illustrates a validated build with compliance chain in accordance with an illustrative embodiment.

FIG. 5 illustrates a validated build with compliance chain in accordance with an illustrative embodiment. In the depicted example, an offering owner 510 sends a build order to cloud operations 520, which forwards the build order to compliance chain 530. In turn compliance chain 530 stores the order in evidence repository (blockchain) 550. Compliance chain 530 then returns the build order event to cloud ops 520, which then begins to build an asset. The cloud ops 520 sends captured evidence records to compliance chain 530, which attaches evidence records as assets to the evidence (compliance) repository 550.

Compliance attester 540 reviews evidence records and returns approval to compliance chain 530. The approval or validation (certification) is stored in evidence repository 550. The compliance chain 530 sends validation to cloud ops 520, at which point the build is complete. Cloud ops 520 sends a build completed event to offering owner 510, at which point, the build is completed and validated.

The illustrative embodiments define a healthcare cloud ops compliance business model containing the participants, assets, actions, states, events, and queries required. The illustrative embodiments apply the above model into a cloud operational design that combines HyperLedger Fabric, Composer, Peer Networks, Smart Contracts, Compliance Data Repository, User Experiences to support the healthcare cloud ops compliance business model. The healthcare cloud ops compliance business model supports dynamic allocation of cloud resources. In addition, the blockchain design ensures compliance to healthcare regulations.

Figure 6:
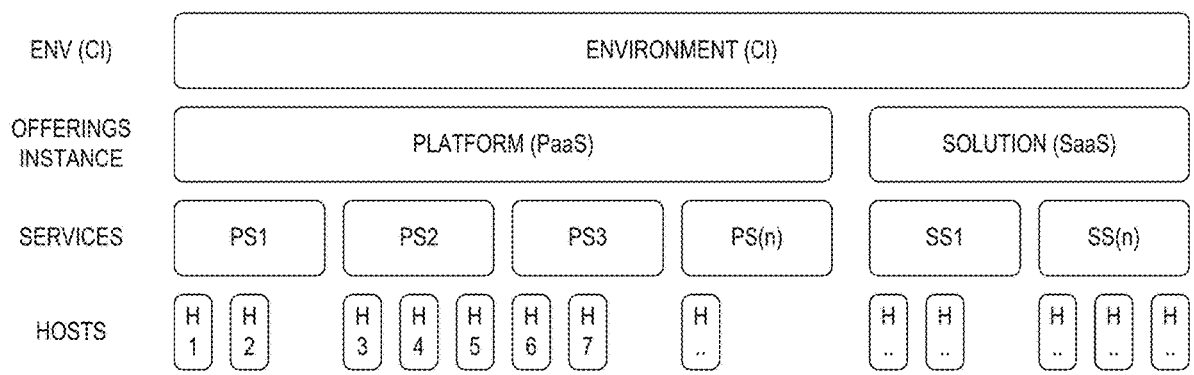
FIG. 6 is a block diagram illustrating healthcare cloud assets in accordance with an illustrative embodiment.

FIG. 6 is a block diagram illustrating healthcare cloud assets in accordance with an illustrative embodiment. The cloud assets include the environment configuration item (CI), offerings instance, services, and hosts. The offerings instance includes the platform (e.g., platform-as-a-service (PaaS)) and solution (e.g., solution-as-a-service (SaaS)). The platform includes one or more platform services (e.g., PSI, ..., PS(n)). The solution includes one or more solution services (e.g., SS1, ..., SS(n)). Each platform service or solution service includes one or more hosts (e.g., H1, ..., H(n)).

The business network details comprise a plurality of internal participants, which may include the following:
Offering Owner
Offering Dev & QA
CloudOps Engineer
Compliance QA The business network details comprise a plurality of external participants, which may include the following:
Solution Business Owner
Regulatory Auditor The business network details comprise a plurality of assets, which may include the following:
Environment
Offering
Service (Component)
Host
Order The business network details comprise a plurality of actions/transactions, which may include the following:
PlaceOrder
Create
Deploy
Reset
Retire
UpdateOrder (modify)
Operationalize
Activate
Deactivate The business network details comprise a plurality of states, which may include the following:
Order
In-Progress
Failed
Completed
Asset
Active
Inactive The business network details comprise a plurality of events, which may include the following:
OrderSubmittedEvent
OrderUpdatedEvent
CompletedOrderEvent
AssetBuiltEvent
AssetRetiredEvent
AssetResetEvent The business network details comprise a plurality of queries/historian details, which may include the following:
Quality Evidence Record
Compliance Analysis Report
Asset History Report In accordance with example embodiments, HyperLedger (i.e., blockchain) fabric technology is leveraged as a cloud-native foundation for healthcare regulatory and compliance operational requirements. The illustrative embodiments use HyperLedger Applications/APIs for each persona (participant) in the business model, HyperLedger Smart Contracts to enforce business compliance rules, and HyperLedger scoped-chains ledgers visible to roles in business model. The illustrative embodiments use persistent storage to capture and safe-keep evidence for compliance and use evidence/test case validation automation using Smart Contracts and Rules. HyperLedgers provide trust, transparency, and accountability. HyperLedgers are also fast, secure, scalable, distributed/resilient, and immutable.

Figure 7:
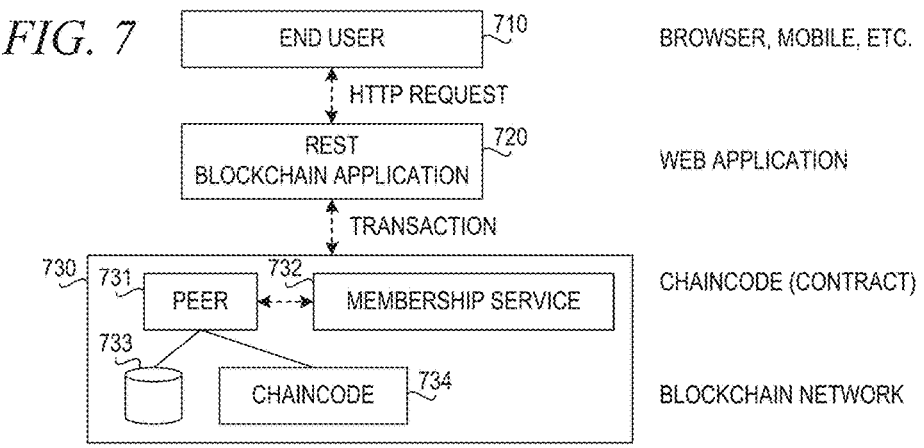
FIG. 7 is a block diagram illustrating a front-end application in accordance with an illustrative embodiment.

FIG. 7 is a block diagram illustrating a front-end application in accordance with an illustrative embodiment. End user 710 sends HyperText Transport Protocol (HTTP) request to blockchain application 720. End user 710 may be a Web browser, mobile device, etc. Blockchain application 720 may be a Web application and use Representational State Transfer (REST) API. Blockchain application 720 sends transactions to blockchain network 730, which includes peer 731, membership service 732, ledger 733, and chaincode 734.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
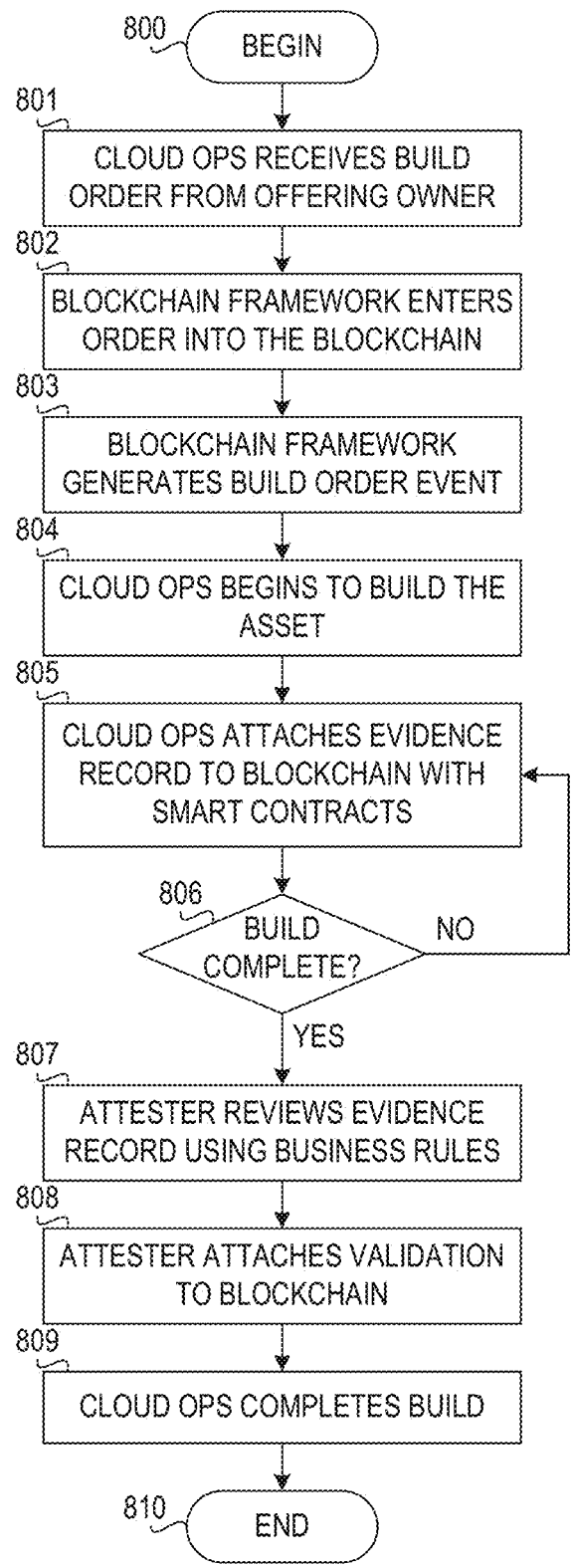
FIG. 8 is a flowchart illustrating operation of a blockchain framework for enforcing regulatory compliance in healthcare cloud solutions in accordance with an illustrative embodiment.

FIG. 8 is a flowchart illustrating operation of a blockchain framework for enforcing regulatory compliance in healthcare cloud solutions in accordance with an illustrative embodiment. Operation begins (block 800), and the cloud ops receives a build order from the offering owner (block 801). The blockchain framework enters the order into the blockchain (block 802). The blockchain framework then generates a build order event (block 803). The cloud ops then begin to build the asset (block 804).

The cloud ops attaches' evidence records to the blockchain using smart contracts (block 805). The blockchain framework determines whether the build is complete (block 806). If the build is not complete, then operation returns to block 805, and the cloud ops continues to attach evidence records to the blockchain.

If the build is complete in block 806, then the compliance attester reviews the evidence records using business rules (block 807). The attester attaches a validation, based on results of reviewing the evidence records, to the blockchain (block 808). Then, the cloud ops completes the build (block 809), and operation ends (block 810).

Figure 9:
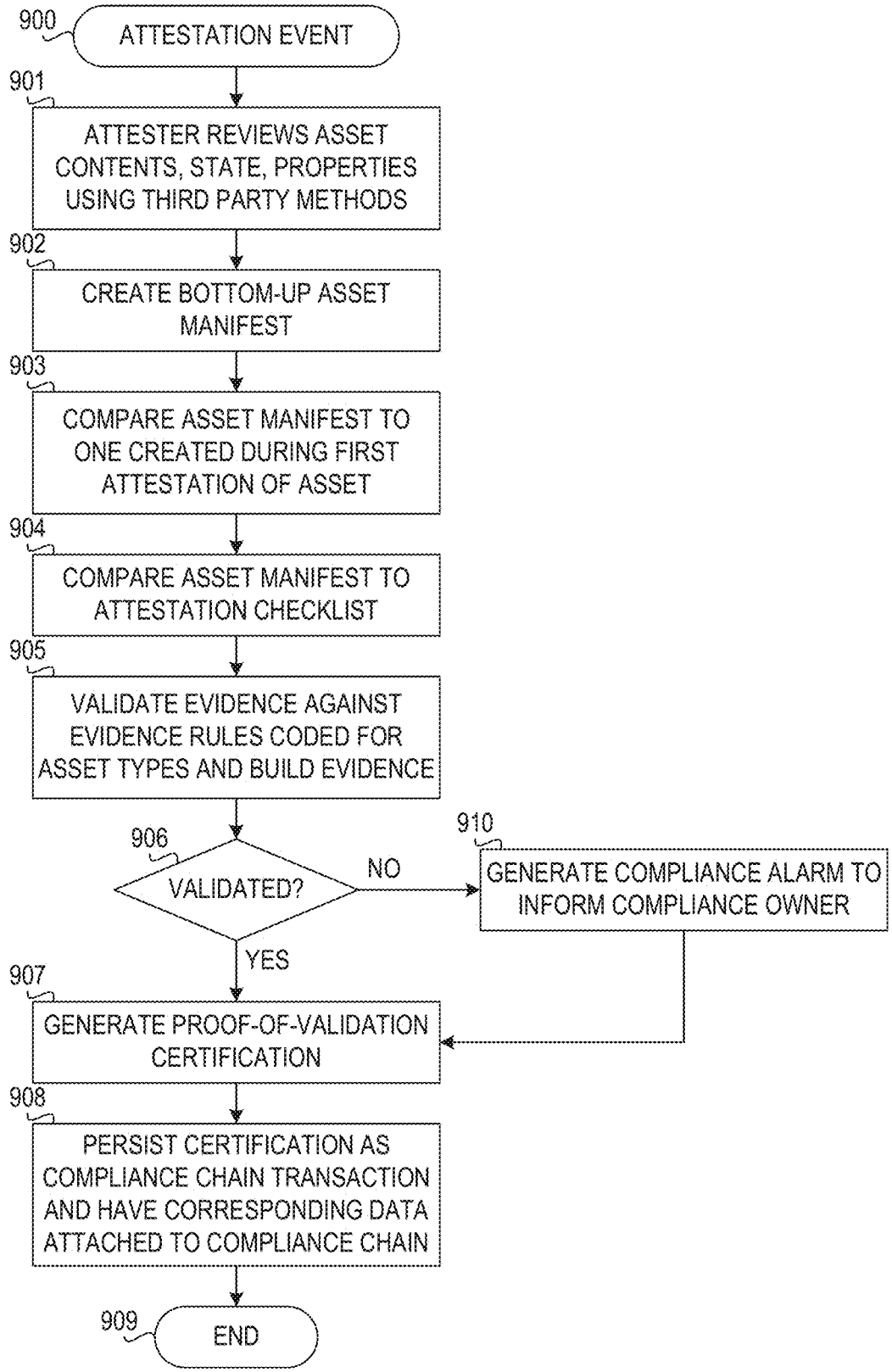
FIG. 9 is a flowchart illustrating operation of a compliance attestation engine in accordance with an illustrative embodiment.

FIG. 9 is a flowchart illustrating operation of a compliance attestation engine in accordance with an illustrative embodiment. Operation begins when an attestation (or re-attestation) event is generated for an asset (block 900). An attestation event may be generated in response to an asset being created, completed, or changed, for example. The compliance attestation engine, or attester, reviews the asset contents, state, properties using third party methods (block 901). The attester creates a bottom-up asset manifest (block 902) and compares the asset manifest to one created during the first attestation of the asset (block 903) to compare what actually got build to what should have been built.

The attester also compares the asset manifest to an attestation checklist of all evidence that should be part of that specific built asset (block 904). The attester validates the evidence against evidence rules coded for asset types and build evidence (block 905). The attester then determines whether the asset is validated (block 906). If the asset is validated, the attester generates a proof-of-validation certification (block 907) and persists the certification as a compliance chain transaction and attaches corresponding (hashed) data to the compliance chain (block 908). Thereafter, operation ends (block 909).

If the attester determines that the asset is not validated in block 906, then the attester generates a compliance alarm to inform the compliance owner (block 910). Then, operation proceeds to block 907, and the attester generates the proof-of-validation certificate indicating the asset is not validated. The attester persists the certification as a compliance chain transaction and attaches corresponding (hashed) data to the compliance chain (block 908). Thereafter, operation ends (block 909).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 10:
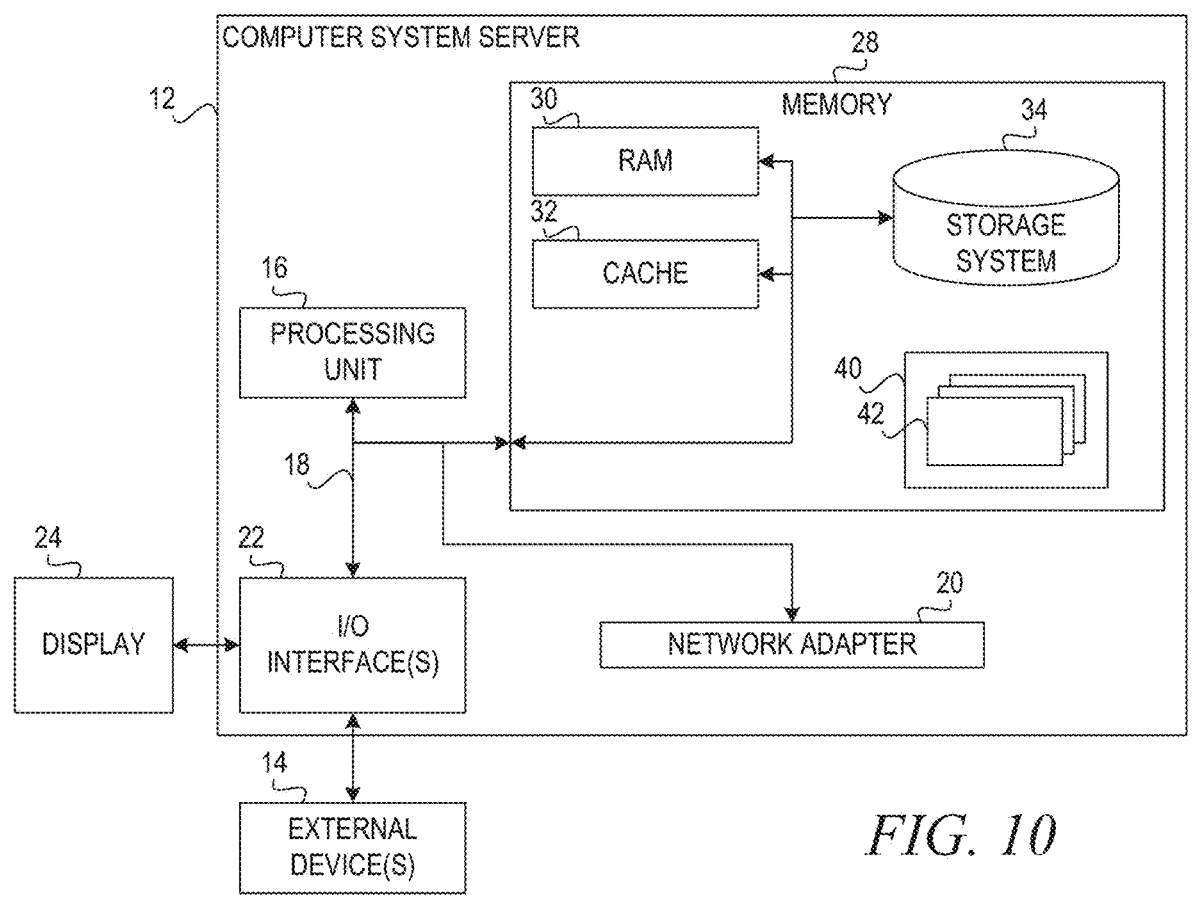
FIG. 10 depicts a cloud computing node according to an illustrative embodiment.

Referring now to FIG. 10, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 11:
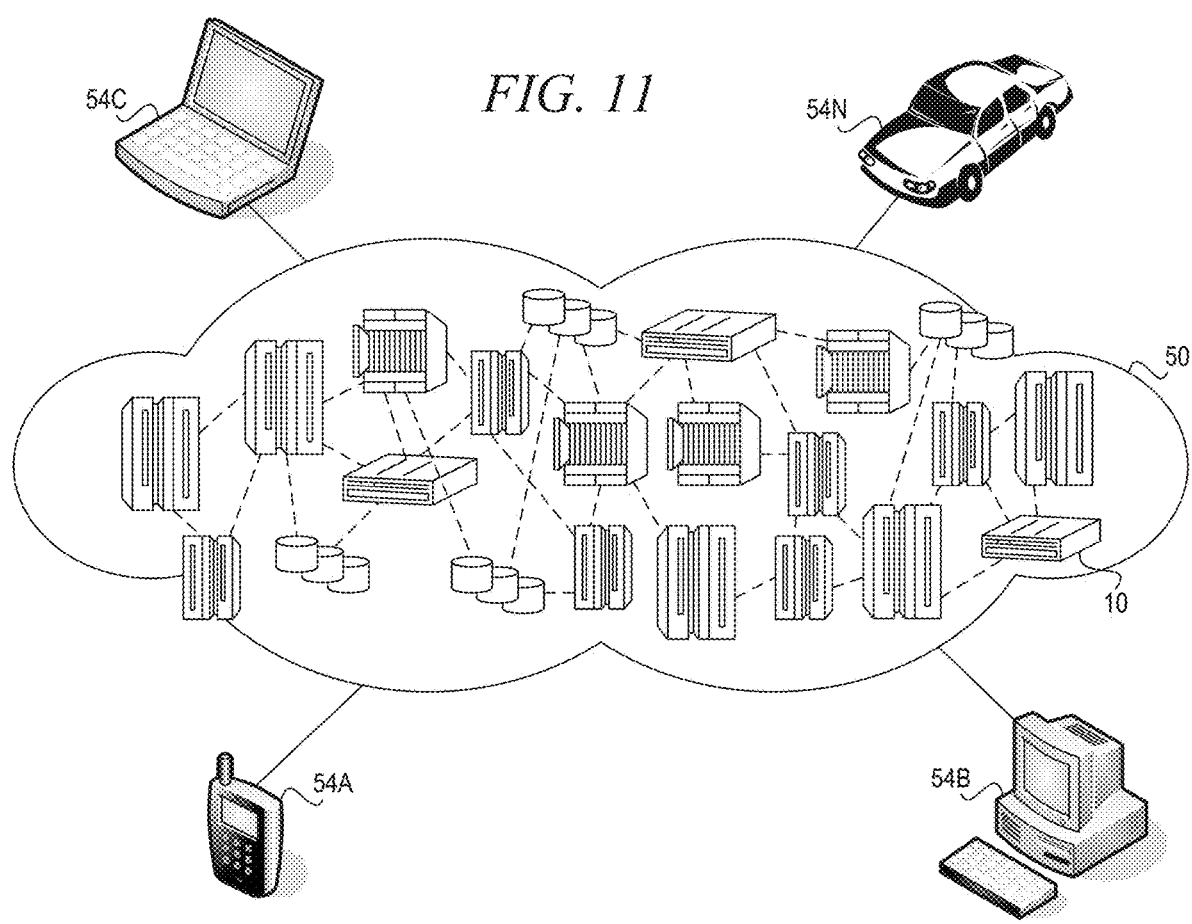
FIG. 11 depicts a cloud computing environment according an illustrative embodiment.

Referring now to FIG. 11, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 11 are intended to be illustrative only and that computing nodes 10 and cloud computing environment 50 can communicate with any type of computerized device over any type of network and/or network addressable connection (e.g., using a web browser).

Figure 12:
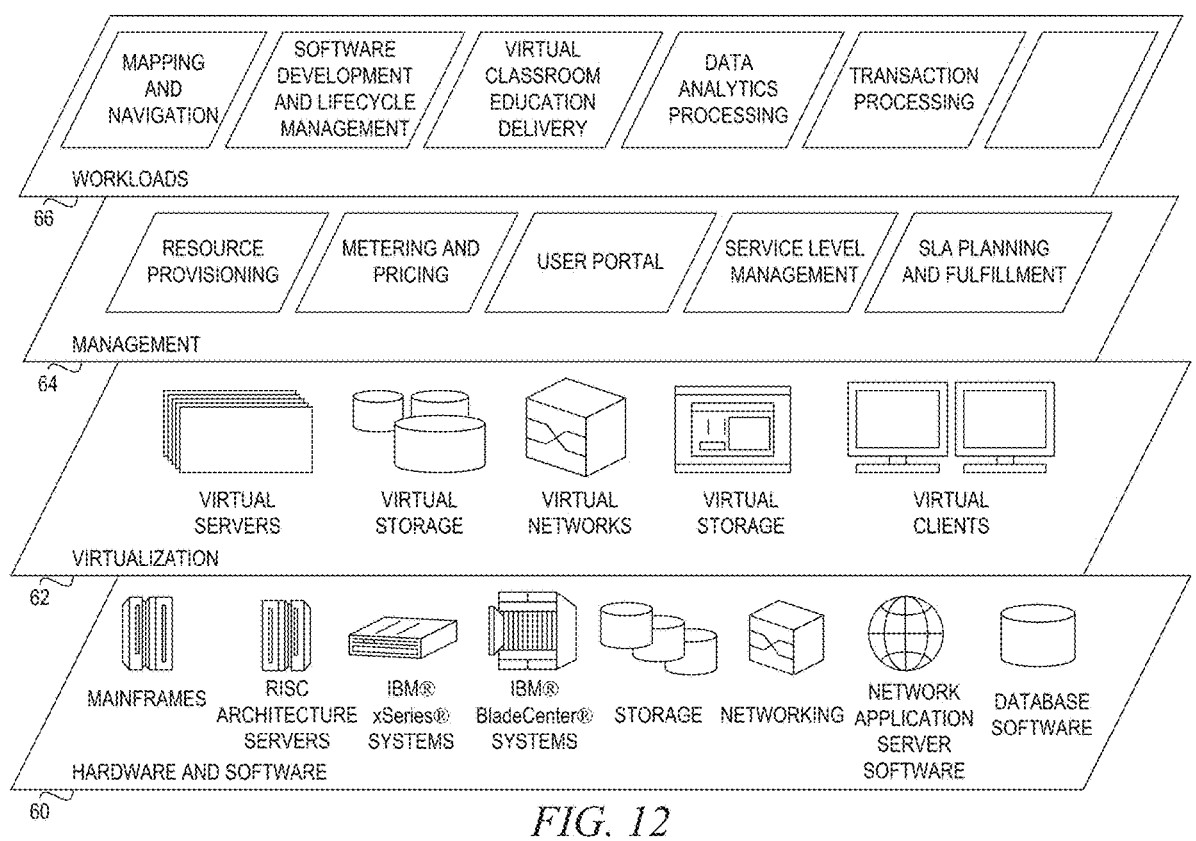
FIG. 12 depicts abstraction model layers according to an illustrative embodiment.

Referring now to FIG. 12, a set of functional abstraction layers provided by cloud computing environment 50 (FIG. 11) is shown. It should be understood in advance that the components, layers, and functions shown in FIG. 12 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; and transaction processing.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions which are executed by the at least one processor and configure the processor to implement a healthcare blockchain framework for continuous compliance auditing readiness and attestation in healthcare cloud solutions, the method comprising:

providing a healthcare blockchain framework to create, read, update, and delete elements of a healthcare compliance model supporting a dynamic allocation of cloud resources to a healthcare business network, wherein compliance with one or more healthcare regulations is built into the blockchain framework;

responsive to an attestation event, reviewing, by a compliance attestation component within the healthcare blockchain framework, asset contents, state, and properties of an asset in a compliance repository;

creating, by the compliance attestation component, a bottom-up asset manifest for the asset;

comparing, by the compliance attestation component, the asset manifest to a test case corresponding to an asset class of the asset;

validating, by the compliance attestation component, the asset against evidence rules corresponding to the asset class of the asset based on the comparison; and responsive to the compliance attestation component validating the asset, generating a proof-of-validation certification.

2. The method of claim 1, further comprising persisting the proof-of-validation certification with an attached hash in the compliance repository as a compliance chain transaction.

3. The method of claim 1, further comprising generating a compliance alarm responsive to the asset not being validated.

4. The method of claim 1, wherein the test case comprises a previous asset manifest created during a previous validation of the asset.

5. The method of claim 1, wherein the test case comprises an attestation checklist for the asset corresponding to the asset class.

6. The method of claim 1, wherein comparing the asset manifest to the test case comprises comparing what actually got built to what should have been built in the asset.

7. The method of claim 1, wherein the attestation event comprises a change to the asset in the compliance repository.

8. The method of claim 1, wherein the evidence rules are coded into the blockchain framework.

9. The method of claim 1, wherein the evidence rules are from third party sources.

10. An apparatus comprising:
at least one processor; and
a memory coupled to the at least one processor, wherein the memory comprises instructions which, when executed by the at least one processor, cause the processor to implement a blockchain framework for continuous compliance auditing readiness and attestation in healthcare cloud solutions, wherein the instructions cause the at least one processor to:
provide a healthcare blockchain framework to create, read, update, and delete elements of a healthcare compliance model supporting a dynamic allocation of cloud resources to a healthcare business network, wherein compliance with one or more healthcare regulations is built into the blockchain framework;
responsive to an attestation event, review, by a compliance attestation component within the healthcare blockchain framework, asset contents, state, and properties of an asset in a compliance repository;
create, by the compliance attestation component, a bottom-up asset manifest for the asset;
compare, by the compliance attestation component, the asset manifest to a test case corresponding to an asset class of the asset;
validate, by the compliance attestation component, the asset against evidence rules corresponding to the asset class of the asset based on the comparison; and
responsive to the compliance attestation component validating the asset, generate a proof-of-validation certification.

11. The apparatus of claim 10, wherein the instructions cause the at least one processor to persist the proof-of-validation certification with an attached hash in the compliance repository as a compliance chain transaction.

12. The apparatus of claim 10, wherein the instructions cause the at least one processor to generate a compliance alarm responsive to the asset not being validated.

13. The apparatus of claim 10, wherein the test case comprises a previous asset manifest created during a previous validation of the asset.

14. The apparatus of claim 10, wherein the test case comprises an attestation checklist for the asset corresponding to the asset class.

15. The apparatus of claim 10, wherein comparing the asset manifest to the test case comprises comparing what actually got built to what should have been built in the asset.

16. The apparatus of claim 10, wherein the attestation event comprises a change to the asset in the compliance repository.

17. The apparatus of claim 10, wherein the evidence rules are coded into the blockchain framework.

18. The apparatus of claim 10, wherein the evidence rules are from third party sources.

19. A computer program product comprising a computer readable storage medium having a computer readable program stored therein, wherein the computer readable program, when executed on a computing device, causes the computing device to implement a blockchain framework for continuous compliance auditing readiness and attestation in healthcare cloud solutions, wherein the computer readable program causes the computing device to:
provide a healthcare blockchain framework to create, read, update, and delete elements of a healthcare compliance model supporting a dynamic allocation of cloud resources to a healthcare business network, wherein compliance with one or more healthcare regulations is built into the blockchain framework;
responsive to an attestation event, review, by a compliance attestation component within the healthcare blockchain framework, asset contents, state, and properties of an asset in a compliance repository;
create, by the compliance attestation component, a bottom-up asset manifest for the asset;
compare, by the compliance attestation component, the asset manifest to a test case corresponding to an asset class of the asset;
validate, by the compliance attestation component, the asset against evidence rules corresponding to the asset class of the asset based on the comparison; and
responsive to the compliance attestation component validating the asset, generate a proof-of-validation certification.

20. The computer program product of claim 19, wherein the computer readable program causes the computing device to persist the proof-of-validation certification with an attached hash in the compliance repository as a compliance chain transaction.

* * * * *